US006464684B1

(12) United States Patent
Galdonik

(10) Patent No.: US 6,464,684 B1
(45) Date of Patent: *Oct. 15, 2002

(54) CATHETER HAVING REGIONS OF DIFFERING BRAID DENSITIES AND METHODS OF MANUFACTURE THEREFOR

(75) Inventor: Jason A. Galdonik, Brooklyn Park, MN (US)

(73) Assignee: SciMed Life Systems, Inc., Maple Grove, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 53 days.

(21) Appl. No.: 09/150,222

(22) Filed: Sep. 9, 1998

(51) Int. Cl.[7] .............................................. A61M 25/00
(52) U.S. Cl. ...................................................... 604/527
(58) Field of Search ................................ 604/523–527, 604/530, 532, 533, 534, 284

(56) References Cited

U.S. PATENT DOCUMENTS

| | | |
|---|---|---|
| 3,416,531 A | 12/1968 | Edwards |
| 3,485,234 A | 12/1969 | Stevens |
| 3,612,058 A | 10/1971 | Ackerman |
| 4,210,478 A | 7/1980 | Shoney |
| 4,385,635 A | 5/1983 | Ruiz |
| 4,419,095 A | 12/1983 | Nebergall et al. |
| 4,516,970 A | 5/1985 | Kaufman et al. |
| 4,516,972 A | 5/1985 | Samson |
| 4,531,943 A | 7/1985 | Van Tassel et al. |
| 4,563,181 A | 1/1986 | Wijayarathna et al. |
| 4,588,399 A | 5/1986 | Nebergall et al. |
| 4,636,346 A | 1/1987 | Gold et al. |
| 4,639,252 A | 1/1987 | Kelly et al. .................. 604/282 |
| 4,690,175 A | 9/1987 | Ouchi et al. |

(List continued on next page.)

FOREIGN PATENT DOCUMENTS

| | | |
|---|---|---|
| EP | 0 180 348 B1 | 5/1986 |
| EP | 0 277 366 A1 | 1/1987 |
| EP | 0 382 974 A1 | 8/1990 |
| EP | 0 473 045 A1 | 8/1990 |
| EP | 0 555 088 A3 | 8/1993 |
| EP | 0 555 088 A2 | 8/1993 |
| EP | 0 810 003 A3 | 12/1997 |
| EP | 0 810 003 A1 | 12/1997 |
| WO | WO 92/15356 | 9/1992 |

OTHER PUBLICATIONS

Kolobow et al., "A new thin–walled nonkinking catheter for peripheral vascular cannulation", *Surgery*, vol. 68, No. 4, Oct., 1970, pp. 625–629.

Primary Examiner—Manuel Mendez
Assistant Examiner—Michael M. Thompson
(74) Attorney, Agent, or Firm—Crompton, Seager & Tufte, LLC

(57) ABSTRACT

A tubing assembly and method of manufacture for a catheter having an inner tubular member defining a lumen, an outer tubular member surrounding said inner member, and a braid mounted between the tubular members to provide rigidity to the flexible catheter. The braid preferably has different braid densities in selected regions along the length of the catheter. In addition, the outer tubular member preferably includes a number of segments each having different mechanical properties. In this configuration, both the polymer characteristics and the braid density may be independently varied along the length of the catheter to maximize catheter performance.

18 Claims, 8 Drawing Sheets

U.S. PATENT DOCUMENTS

| | | |
|---|---|---|
| 4,705,511 A | 11/1987 | Kocak |
| 4,735,620 A | 4/1988 | Ruiz |
| 4,817,613 A | 4/1989 | Jaraczewski et al. |
| 4,838,879 A | 6/1989 | Tanabe et al. |
| 4,842,590 A | 6/1989 | Tanabe et al. |
| 4,863,442 A | 9/1989 | DeMello et al. |
| 4,898,591 A | 2/1990 | Jang et al. |
| 4,899,787 A | 2/1990 | Ouchi et al. |
| 5,017,259 A | 5/1991 | Kohsai |
| 5,057,092 A | 10/1991 | Webster, Jr. |
| 5,069,674 A | 12/1991 | Fearnot et al. |
| 5,078,702 A | 1/1992 | Pomeranz |
| 5,160,559 A | 11/1992 | Scovil et al. |
| 5,163,431 A | 11/1992 | Griep |
| 5,176,660 A | 1/1993 | Truckai |
| 5,180,376 A | 1/1993 | Fischell |
| 5,190,520 A | 3/1993 | Fenton, Jr. et al. |
| 5,217,440 A | 6/1993 | Frassica |
| 5,221,270 A | 6/1993 | Parker |
| 5,221,372 A | 6/1993 | Olson |
| 5,222,949 A | 6/1993 | Kaldany |
| 5,234,416 A | 8/1993 | Macaalay et al. |
| 5,254,107 A | 10/1993 | Soltesz |
| 5,279,596 A | 1/1994 | Castaneda et al. |
| 5,306,252 A | 4/1994 | Yuteri et al. |
| 5,308,342 A | 5/1994 | Sepetka et al. |
| 5,335,305 A | 8/1994 | Kosa et al. |
| 5,358,493 A | 10/1994 | Schweich, Jr. et al. |
| 5,423,773 A | 6/1995 | Jimenez |
| 5,423,774 A | 6/1995 | Fischell et al. |
| 5,445,624 A | 8/1995 | Jimenez |
| 5,509,910 A | 4/1996 | Lunn |
| 5,514,108 A | 5/1996 | Stevens |
| 5,538,513 A * | 7/1996 | Okajima ............... 604/523 |
| 5,545,151 A | 8/1996 | O'Connor et al. |
| 5,569,218 A | 10/1996 | Berg |
| 5,599,319 A | 2/1997 | Stevens |
| 5,603,705 A | 2/1997 | Berg |
| 5,658,263 A | 8/1997 | Dang et al. |
| 5,674,208 A | 10/1997 | Berg et al. |
| 5,676,659 A | 10/1997 | McGurk |
| 5,702,373 A * | 12/1997 | Samson ............... 604/527 |
| 5,711,909 A | 1/1998 | Gore et al. ............ 264/320 |
| 5,725,513 A * | 3/1998 | Ju et al. .............. 604/523 |
| 5,738,742 A * | 4/1998 | Stevens ............... 156/149 |
| 5,827,242 A * | 10/1998 | Follmer et al. ........ 604/524 |
| 5,964,971 A * | 10/1999 | Lunn .................. 156/86 |
| 5,972,143 A * | 10/1999 | Stevens ............... 156/149 |

\* cited by examiner

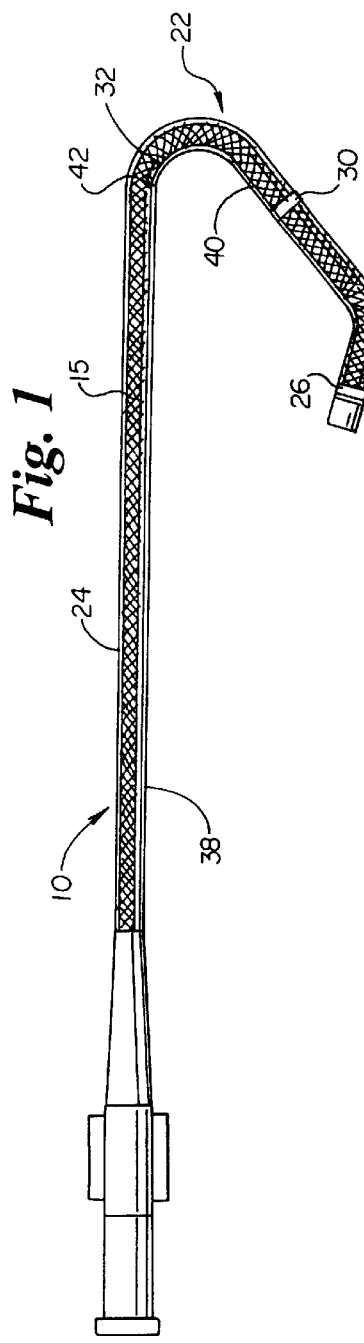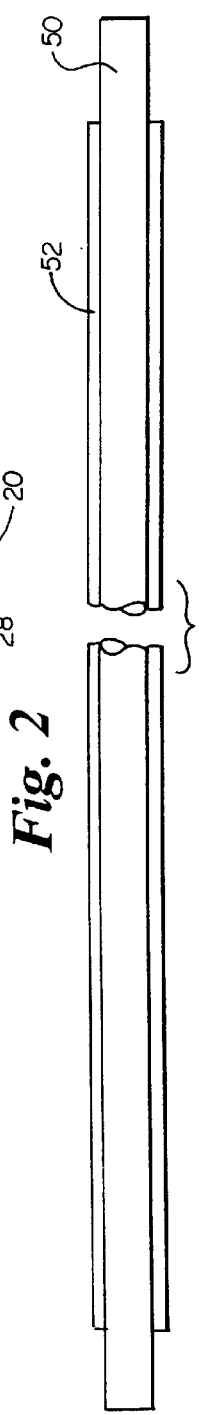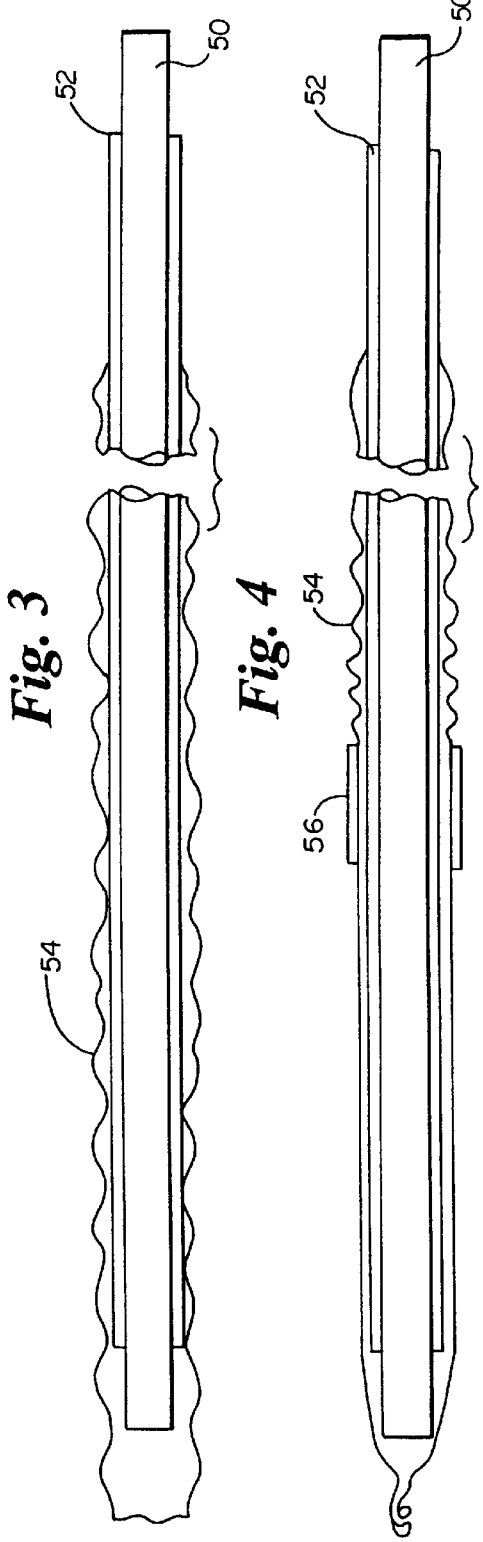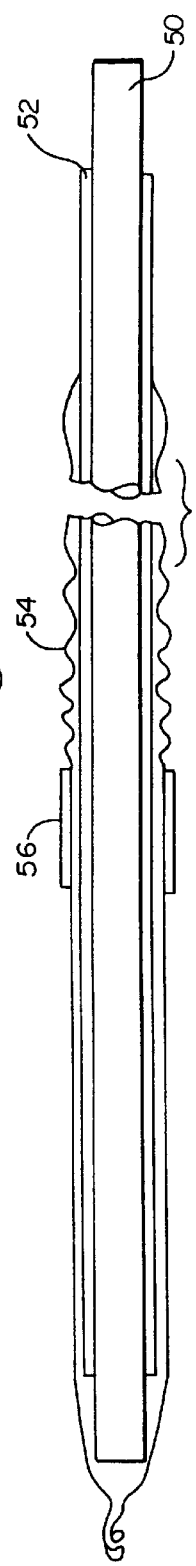
Fig. 1
Fig. 2
Fig. 3
Fig. 4

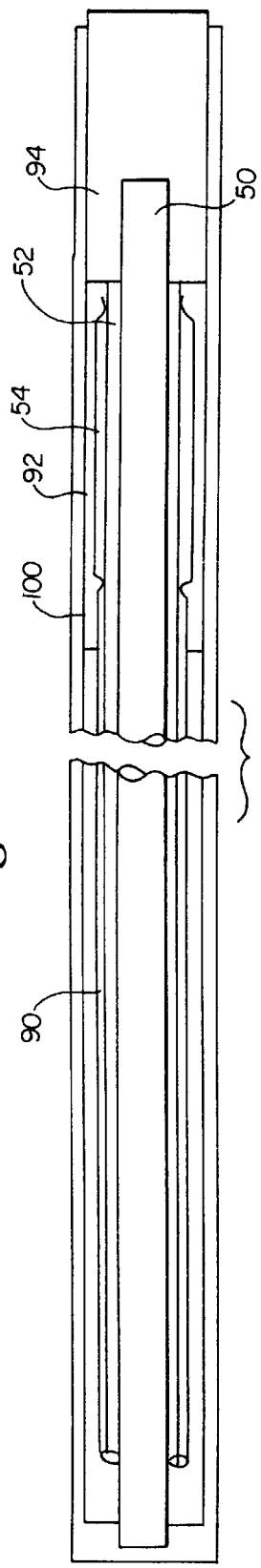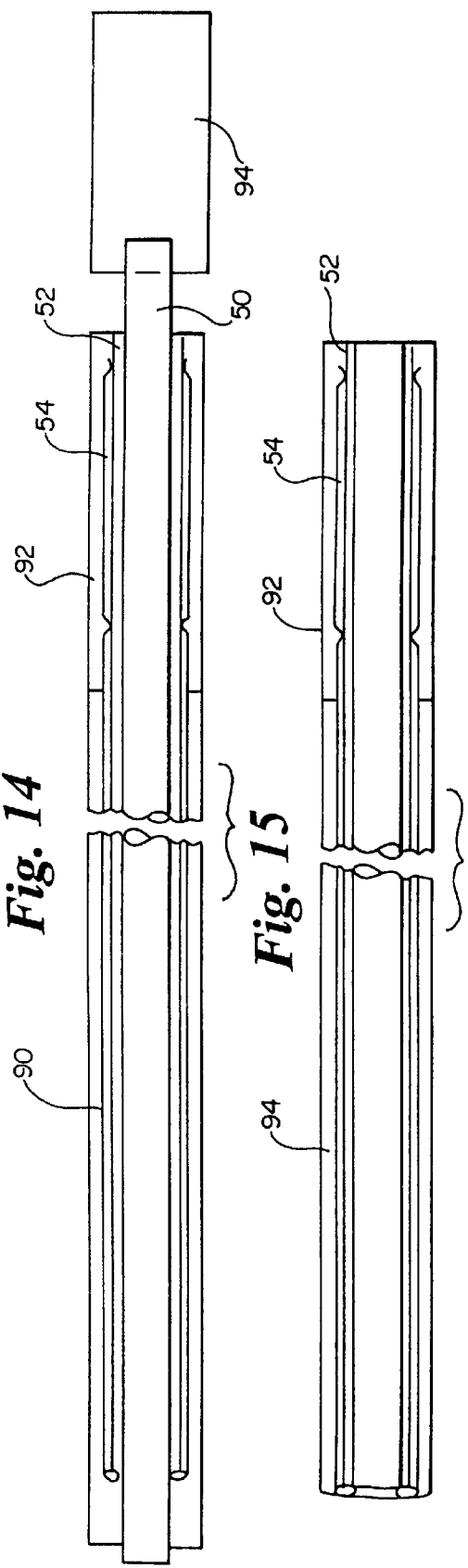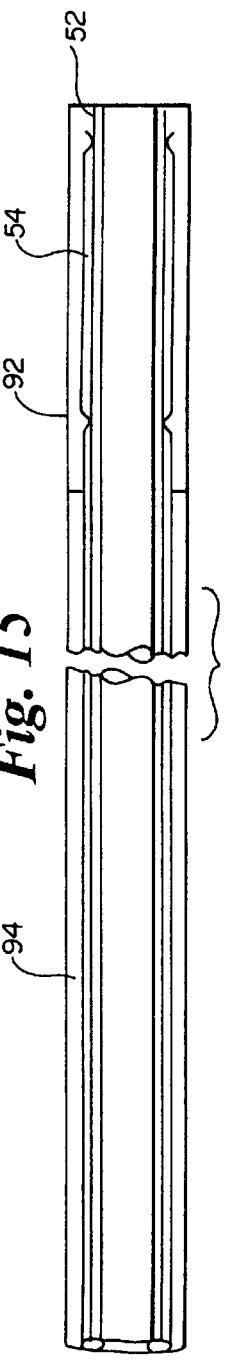
Fig. 13
Fig. 14
Fig. 15

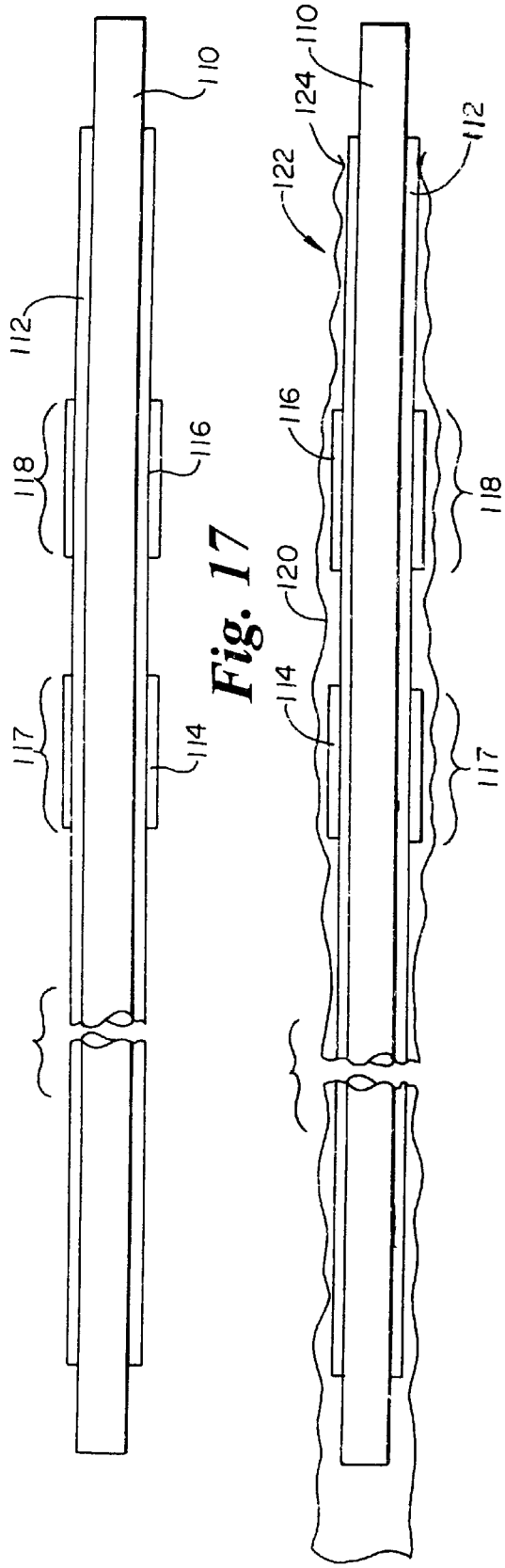
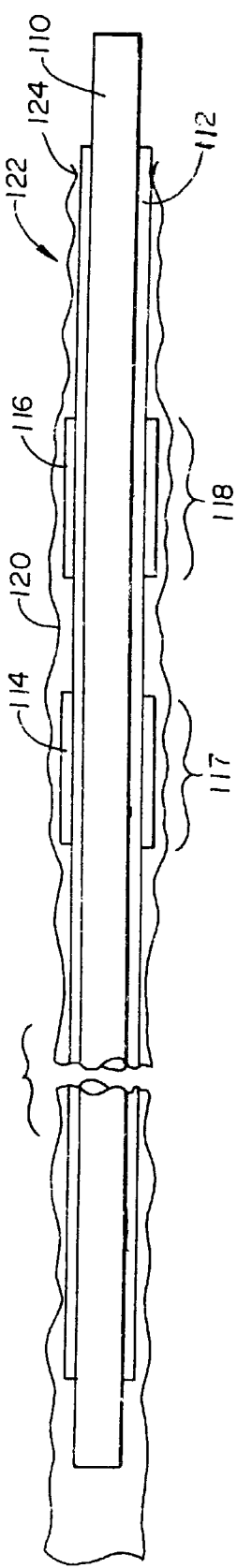
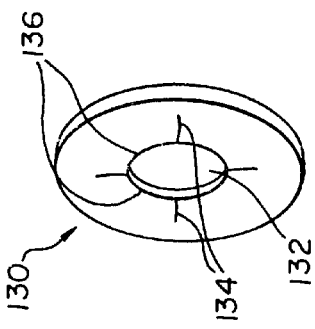

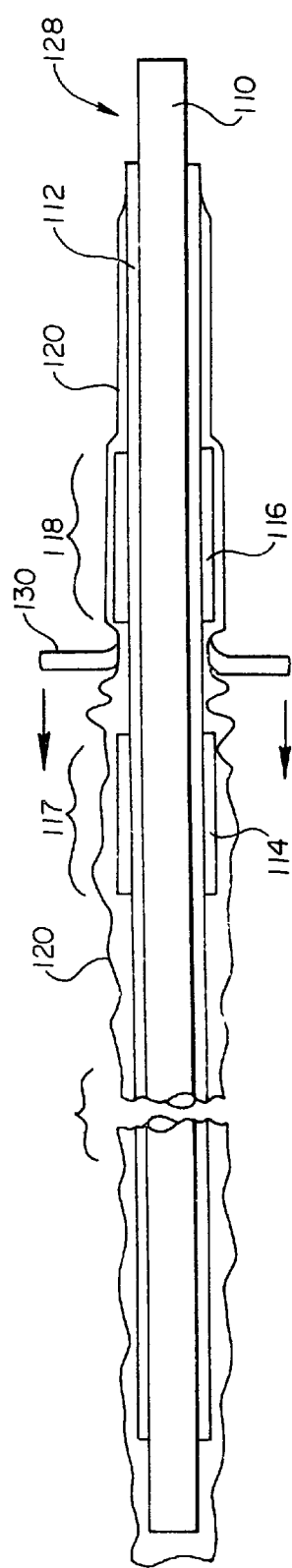
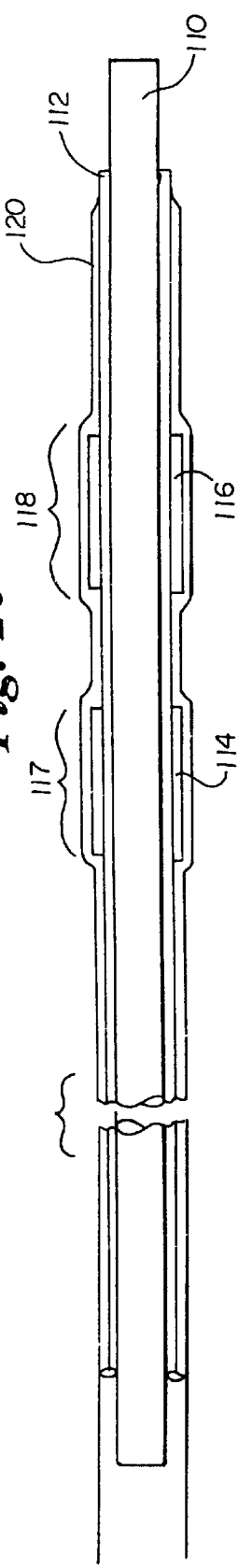

US 6,464,684 B1

CATHETER HAVING REGIONS OF DIFFERING BRAID DENSITIES AND METHODS OF MANUFACTURE THEREFOR

CROSS REFERENCES TO CO-PENDING APPLICATIONS

This application is related to U.S. patent application Ser. No. 08/936,983 filed Sep. 25, 1997, entitled "Catheter Having a High Tensile Strength Braid Wire Constraint and Method of Manufacture", which is a continuation-in-part of U.S. patent application Ser. No. 08/800,926 filed Feb. 13, 1997, entitled "Catheter Having an Adhesive Braid Wire Constraint and Method of Manufacture", which is a continuation-in-part of U.S. Pat. No. 5,603,705 filed Aug. 15, 1995, entitled "Catheter Joint with Restraining Device", which is a continuation of U.S. patent application Ser. No. 08/171,925, filed Dec. 22, 1993, entitled "Catheter Joint with Restraining Device", both of which are related to U.S. patent application Ser. No. 08/108,973, filed Aug. 18, 1993, entitled "Improved Thin-Walled Catheter", all assigned to the assignee of the present invention, which disclosures are all incorporated herein by reference. This application is also related to U.S. patent application Ser. No. 08/800,927 filed Feb. 13, 1997, entitled "Guide Catheter Having Selected Flexural Modulus Segrnents", which is a continuation-in-part of U.S. patent application Ser. No. 08/703,635, filed Aug. 27, 1996, entitled "Guide Catheter Having a Plurality of Filled Distal Grooves", which is a continuation-in-part of U.S. patent application Ser. No. 08/195,222, filed Feb. 14, 1994, entitled "Elastic Guide Catheter Transition Element" now issued as U.S. Pat. No. 5,569,218, all assigned to the assignee of the present invention, the disclosures of which are all incorporated herein by reference.

TECHNICAL FIELD

The present invention generally relates to the field of medical devices, and more particularly, to the field of catheters such as guide catheters used for the placement of medicines and medical devices within the body and diagnostic catheters used to inject radiopaque fluids within the body for treatment and diagnosis of vascular diseases. Specifically, the invention is directed to a catheter tube, particularly useful in intravascular guide catheters, incorporating regions of different braid density and/or material characteristics, and methods of manufacture therefor.

BACKGROUND OF THE INVENTION

The use of intravascular catheters for treatment of the body is well known in the field of medicine. The need for a choice of catheter sizes and types has grown rapidly as the techniques for their use have been greatly improved and the types of medical uses have expanded quickly. One such catheter is a guide catheter which includes a tubular member having a lumen therethrough. Guide catheters are commonly used in diagnostic and treatment techniques related to vascular disease such as angioplasty.

A guide catheter is typically inserted into the femoral artery and routed to a location near a treatment or diagnostic site through the aorta over the aortic arch to the ostium of a target vessel. The guide catheter provides a conduit so that fluid or another medical device can be delivered easily to the proximate location of treatment via the lumen of the guide catheter. Prior art catheters often include a tubular member including a pair of congruent tubes, the inner one defining the lumen. A hub is connected at the proximal end of the tubes, which in addition to providing access to the lumen for fluids and the like, is often used to input torque and other necessary pressures to the tubes during their placement within the body. A tip of a selected design is placed at the distal end of the tubes.

In order for the physician to place the catheter at the correct location in the vessel, the physician must apply longitudinal and rotational forces. The catheter must be rigid enough to transmit sufficient force from the proximal end to the distal end, yet flexible enough to navigate the bends in the blood vessel. Further, the catheter must be torsionally rigid to transmit the applied torque and radially rigid to resist kinking. One way to accomplish a balance between longitudinal rigidity and flexibility, while insuring sufficient torque and radial strength, is to provide a support member in the catheter shaft. Typically, the support member is provided between an inner tube and an outer tube to form the catheter shaft.

The support member is often a braid of metal wires or the like. The performance criteria of a catheter can be affected by altering the density (i.e., pic count) of the braid. Specific performance criteria which can be altered include shaft stiffness, curve support, and kink resistance. Altering the braid pic count can affect shaft stiffness by changing the amount of polymer in the catheter shaft and the degree of interstial bonding between the polymer and the inner tube. Altering the braid can also affect curve support in a similar manner. Polymer in the shaft forming the curve provides support and shape memory. In addition, an optimal degree of braid density is required in the curve to provide a degree of flexibility so that the catheter shaft can align coaxially to the engaged artery. Finally, altering the braid pic affects kink resistance. Increasing braid pic will normalize the braid angle to the catheter surface and increase the amount of reinforcing wire in the shaft.

It is possible to construct a device that is very rigid to obtain the correct amount of shaft stiffness and curve support. However, the resulting device may track poorly, be traumatic to the patient's arteries and kink easily due to its rigidity. Similarly, it is possible to construct a very flexible device to increase trackability, limit the trauma the device imparts to the blood vessels and limit kinkability. However, the device then may become too flexible to provide sufficient shaft stiffness and curve support.

SUMMARY OF THE INVENTION

The present invention overcomes many of the disadvantages associated with the prior art by varying the braid density in specific regions of the catheter, thereby optimizing shaft stiffness, curve support and kink resistance. Further, the present invention contemplates placing a number of segments, each having selected mechanical characteristics, at desired locations along the length of the catheter. Accordingly, the present invention may allow both the mechanical characteristics and the braid density to be independently varied along the length of the catheter to help reduce catheter back-out and maximize catheter performance.

In one illustrative embodiment of the present invention, a catheter shaft having a first region and a second region is provided. A support member extends along at least a portion of the catheter shaft including along the first region and the second region. The support member has a first portion that corresponds to the first region of the catheter shaft and a second portion that corresponds to the second region of the catheter shaft. The density of the support member is changed by changing the diameter of the support member in the first portion relative to the second portion. Thus, the first portion of the support member may provide different torsional rigidity, flexibility, and radial strength to the catheter shaft relative to the second portion.

Preferably, the support member is braid that is disposed between an inner layer and outer layer of the catheter shaft. To increase the diameter of the braid, it is contemplated that the inner layer may have an increased diameter in the first region relative to the second region. This may be accomplished in any number of ways, including providing an annulus or short tubular segment of material around the inner layer adjacent the first region, or using a sleeve to selectively increase the density of the braid in the first region, as more fully described below.

It is also contemplated that the outer layer of the catheter shaft may include two or more segments, wherein at least one of the segments includes a material that has different mechanical characteristics than another one of the segments. For example, the catheter may include a first tubular section and a second tubular section, wherein the first tubular section includes a plastic material that has one or more different mechanical properties than the plastic material of the second tubular section. As more fully described in U.S. patent application Ser. No. 08/800,927 filed Feb. 13, 1997, entitled "Guide Catheter Having Selected Flexural Modulus Segments", selected polymers having different characteristics may be used for various regions of the catheter. This may allow the rigidity of the catheter to be increased in discrete segments, thereby increasing the curve resistance while maintaining the flexibility of the catheter. Accordingly, the present invention may allow both the polymer characteristics and the braid density to be independently varied along the length of the catheter for optimal catheter performance.

The present invention also contemplates a number of methods for forming a catheter having a support member with various braid densities along its length. One illustrative method for forming a catheter having an inner tube and a support member includes the steps of: providing the support member over the inner tube; causing a first region of the support member to have a first diameter, wherein the first region has a proximal end and a distal end; securing the support member relative to the inner tube proximate the distal end of the first region; causing a second region of the support member to have a second diameter, wherein the first diameter is different from the second diameter, and wherein the second region overlaps at least a portion of the first region; and securing the support member relative to the inner tube proximate the distal end of the second region. The support member may be secured to the inner tube using any number of techniques including using a suitable adhesive or an annulus of heat shrink tubing.

More specifically, the above method for forming a catheter having an inner tube and a support member may includes the steps of: sliding the support member distally over the outer surface of the inner tube; sliding a first sleeve having a distal end over at least a portion of the support member until the distal end of the first sleeve reaches a first location, the first location being distal of the proximal end of the inner tube; securing the support member relative to the inner tube proximate the first location; removing the first sleeve; sliding a second sleeve having an inner diameter that is less than the inner diameter of the first sleeve over the support member until a distal end of the second sleeve reaches a second location, wherein the second location is proximal of the first location; and securing the support member relative to the inner tube proximate the second location.

Another illustrative method of the present invention for forming a catheter having an inner tube and a support member includes the steps of: forming an inner tube having a first region and a second region, wherein the first region has a first outer diameter and the second region has a second outer diameter; sliding the support member distally over at least a portion of the inner tube including over the first region and the second region; tensioning the support member against the first region and the second region; and providing an outer layer over the support member. Preferably the first region of the inner tube has an increased outer diameter relative to the second region, and is formed by providing an annulus or tubular segment of material around the inner tube over the length of the first region.

These and other various advantages and features of novelty which characterize the present invention are pointed out with particularity in the claims annexed hereto and forming a part hereof However, for a better understanding of the invention, its advantages and the objects obtained by its use, reference should be made to the drawings which form a further part hereof and to the accompanying descriptive matter, in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views:

FIG. 1 is a partial cut-away side view of an illustrative catheter in accordance with the present invention;

FIG. 2 shows a partial cross-sectional side view of a mandrel having an inner layer provided thereon;

FIG. 3 shows a braid provided over the inner layer of FIG. 2;

FIG. 4 shows a first diameter sleeve provided over part of the braid of FIG. 3;

FIG. 13 shows a heat shrink sleeve positioned over the first outer tube, the second outer tube and the plug tube of FIG. 12;

FIG. 14 shows the catheter of FIG. 13, with the heat shrink sleeve removed;

FIG. 15 shows the catheter of FIG. 14 with the proximal and distal ends trimmed;

FIG. 16 shows a partial cross-sectional side view of a mandrel having an inner layer provided thereon, with the two rings provided around the inner layer;

FIG. 17 shows a braid provided over the inner layer and the two rings of FIG. 16;

FIG. 18 shows a perspective view of a grab washer for tensioning the braid of FIG. 17;

FIG. 19 shows the grab washer of FIG. 18 tensioning the braid of FIG. 17; and

FIG. 20 shows the braid fully tensioned over the inner layer and the two ring layers.

DETAILED DESCRIPTION OF PREFERRED EMBODIMENTS

Figure 5:
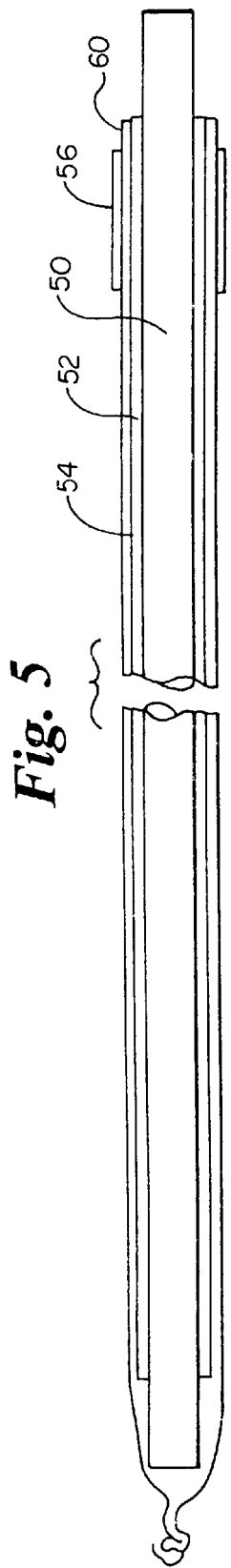
FIG. 5 shows the first diameter sleeve of FIG. 4 in a distal position, exposing only the distal end of the braid.

As required, detailed embodiments of the present invention are disclosed herein. However, it should be understood that the disclosed embodiments are merely exemplary of the present invention which may be embodied in various systems. The discussion with respect to FIG. 1 is directed to a catheter in accordance with an illustrative embodiment of the present invention. The discussion with respect to FIGS. 2–15 is directed to a first method for forming a catheter in accordance with the present invention. The discussion with respect to FIGS. 16–20 is directed to a second method for forming a catheter in accordance with the present invention. It should be recognized, however, that elements of each embodiment and method may be incorporated in a catheter construction in combinations as would be well understood by one skilled in the art. Therefore, specific details disclosed herein are not to be interpreted as limiting, but rather as a basis for the claims and as a representative basis for teaching one skilled in the art to variously practice the present invention.

FIG. 1 shows a guide catheter 10, which may be a thin-walled catheter. Catheter 10 includes an outer tubular member which surrounds and is coaxial with an inner tubular member. The outer tubular member and the inner tubular member are described in more detail below. A support member is positioned between the inner tubular member and the outer tubular member.

The support member may be a braid of metal wire, and may have a first braid density in a first region 20, a second braid density in a second region 22 and a third braid density in a third region 24. While three regions are shown in FIG. 1, it is contemplated that the any number of regions may be used, and the number of regions may be selected based on the desired application of the catheter.

The distal end of the braid 26 is preferably secured to the inner tubular member using an adhesive as disclosed in U.S. patent application Ser. No. 08/936,983 filed Sep. 25, 1997, entitled "Catheter Having a High Tensile Strength Braid Wire Constraint and Method of Manufacture", or via a short sleeve of a heat shrink material such as FEP. The adhesive preferably is a UV cure urethane or epoxy, such as is available from Dymax Corporation in Torrington, Conn.

The braid may also be secured to the inner tubular member at a location 30 between the first region 20 and the second region 22, and at a location 32 between the second region 22 and the third region 24. Preferably, the density of the braid is different in the first region 20, the second region 22 and the third region 24. As more fully described below, the density of the braid may be changed by altering the inner and/or outer diameter of the braid in each of the respective regions. By selecting the appropriate number of regions and the placement of the regions, the flexibility of the catheter may be optimized to reduce the tendency for catheter back-out.

It is also contemplated that the outer tubular member may include a number of segments, each positioned at a desired location along the length of the catheter. Each of the segments may be formed from a material that has different mechanical characteristics relative to the other segments. In the embodiment shown, the outer tubular member includes a first segment 38 and a second segment 40. The first segment is shown joining the second segment at line 42. The material used for the first segment 38 may have one or more properties that differ from the properties of the material used to form the second segment 40. For example, the first segment 38 may be formed from a material that has less flexibility than the material used for the second segment 40. This allows the rigidity of the catheter to be increased at discrete segments. Accordingly, the present invention may allow both the material characteristics of the outer tubular member and the braid density to be independently varied along the length of the catheter to help reduce catheter back-out and maximize catheter performance.

The inner tubular member is preferably formed from polytetrafluroethelene (PTFE), and the outer tubular member is preferably formed from PEBAX. The outer surface of the PTFE inner tubular member is preferably chemical etched so that the braid can more readily be adhered thereto. The chemical etch may also aid the PEBAX outer tubular member to more readily adhere to the inner tubular member when urged through the interstitial spaces of the braid during processing, as more fully described below.

FIGS. 2–15 illustrate a first method for forming a catheter in accordance with the present invention. FIG. 2 shows a mandrel 50 having an inner tubular member 52 provided thereon. The mandrel 50 is preferably made from a stainless steel, and the inner tubular member 52 is preferably made from PTFE. FIG. 3 shows a braid 54 provided over the inner tubular member 52. As shown, the braid 54 is not yet tensioned and therefore has a non-uniform outer diameter. The proximal end of the braid is preferably twisted to anchor the proximal end of the braid relative to the inner tubular member 54, as more clearly shown in FIG. 4.

FIG. 4 also shows a first sleeve 56 having a first inner diameter provided over part of the braid 54. Preferably, the first sleeve 56 is formed from PTFE. As the first sleeve 56 is slid over the braid 54, the braid 54 assumes a constant outer diameter defined by the inner diameter of the first sleeve 56. The diameter of the braid 54 then defines the density of the braid in that region. It has been found for each 0.001" decrease in the outer diameter of the braid 54, the braid density may change by as much as 7 pic.

Figure 6:
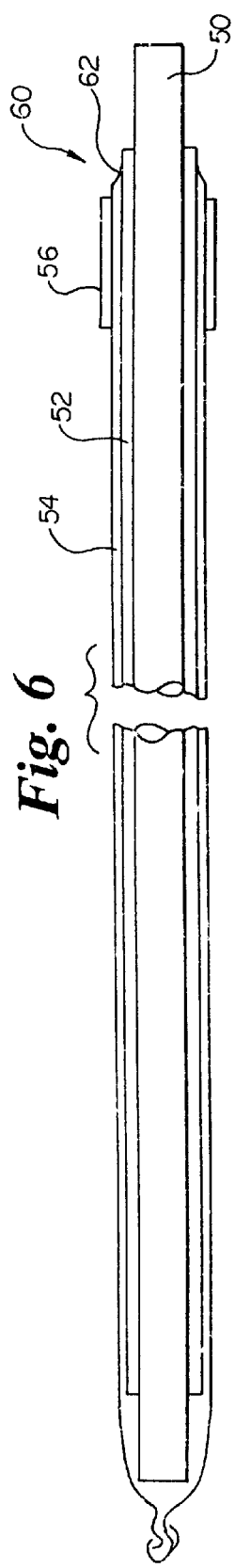
FIG. 6 shows the exposed distal portion of FIG. 5 secured to the inner layer.

FIG. 5 shows the first sleeve 56 slid distally over the braid 54 to a distal position, wherein only the distal end 60 of the braid 54 is exposed. In this position, nearly the entire braid 54 has a constant braid density defined by the inner diameter of the first sleeve 56. With the first sleeve 56 in place, the exposed distal portion 60 of the braid 54 is secured to the inner tubular member 52, as shown in FIG. 6. The distal portion 60 of the braid 54 is preferably secured using a UV cure adhesive or epoxy 62, as disclosed in U.S. patent application Ser. No. 08/936,983 filed Sep. 25, 1997, entitled "Catheter Having a High Tensile Strength Braid Wire Constraint and Method of Manufacture". It is also contemplated that the distal portion 60 of the braid 54 may be secured relative to the inner tubular member 52 using a ring of heat shrink material such as FEP.

Figure 7:
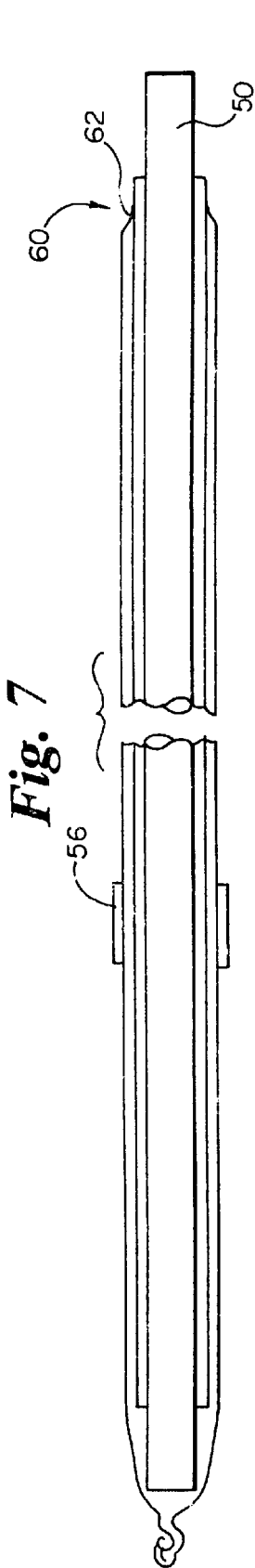
FIG. 7 shows the first diameter sleeve of FIG. 6 partially removed from the braid.
Figure 8:
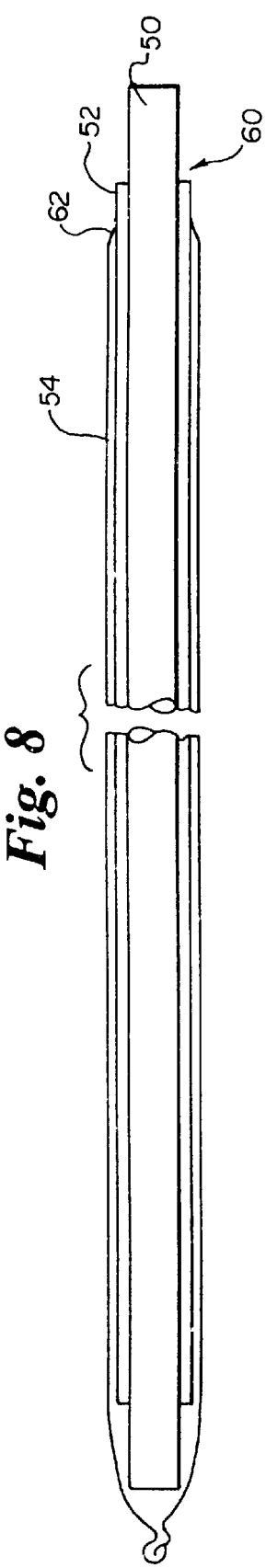
FIG. 8 shows the first diameter sleeve of FIG. 7 completely removed from the braid.

Once the distal portion 60 of the braid 54 is secured relative to the inner tubular member 52, the first sleeve 56 is removed. FIG. 7 shows the first sleeve 56 partially removed, and FIG. 8 shows the first sleeve 56 completely removed.

Figure 9:
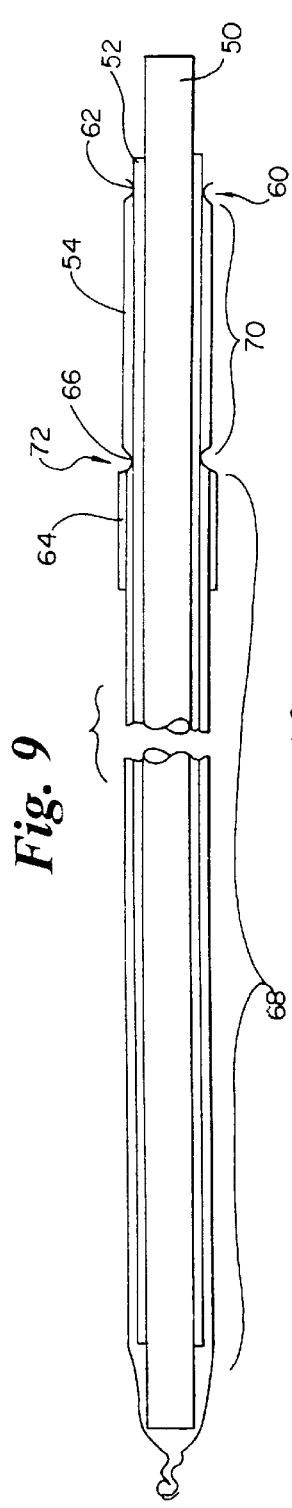
FIG. 9 shows a second diameter sleeve provided over part of the braid of FIG. 8, and the exposed portion of the braid just distal of the second diameter sleeve secured to the inner layer.

FIG. 9 shows a second sleeve 64 provided over a first region 68 of the braid 54. Like the first sleeve 56, the second sleeve 64 is preferably formed from PTFE. However, the second sleeve 64 preferably has a reduced inner diameter relative to the first sleeve 56. In this configuration, as the second sleeve 64 is slid over the braid 54, the braid 54 assumes a reduced outer diameter in a first region 68. This produces a lower braid density in the first region 68. By reducing the diameter and thus the braid count of the braid in the first region 68, the additional braid is pushed into a second region 70. This increases the braid density in the second region 70. As indicated above, it has been found that it is possible to obtain a change of approximately 7 pic for each 0.001" decrease in the outer diameter of the braid 54.

With the second sleeve 64 in place, an intermediate portion 72 of the braid 54 is secured to the inner tubular member 52. The intermediate portion 72 of the braid 54 is secured to the inner tubular member 52 using a UV cure adhesive or epoxy 66, as disclosed in U.S. patent application Ser. No. 08/936,983 filed Sep. 25, 1997, entitled "Catheter Having a High Tensile Strength Braid Wire Constraint and Method of Manufacture". It is also contemplated that the intermediate portion 72 of the braid 54 may be secured relative to the inner tubular member 52 using a ring of heat shrink material such as FEP.

Figure 9A:
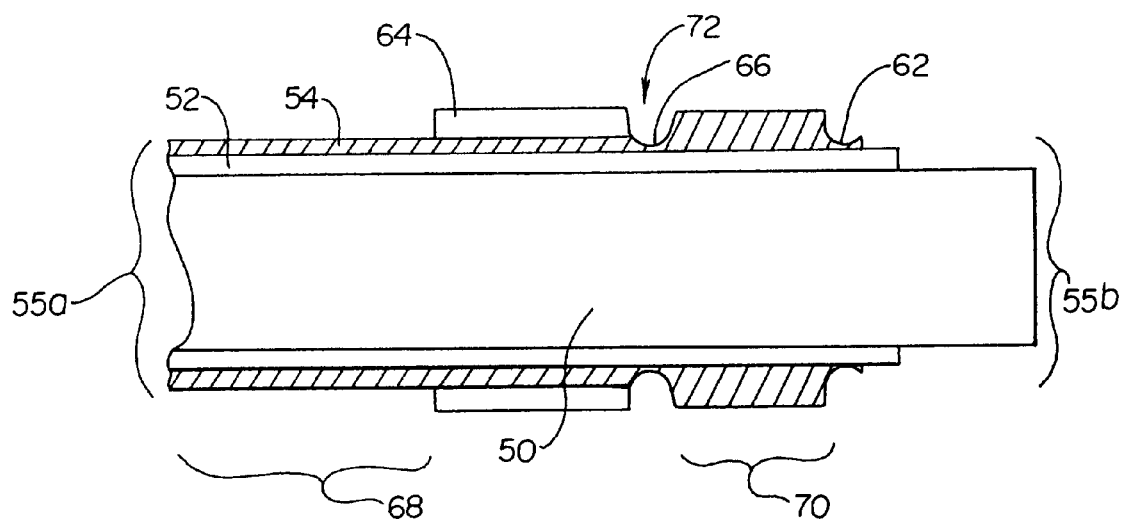
FIG. 9A shows an exaggerated view of an area of interest of FIG. 9.
Figure 9B:
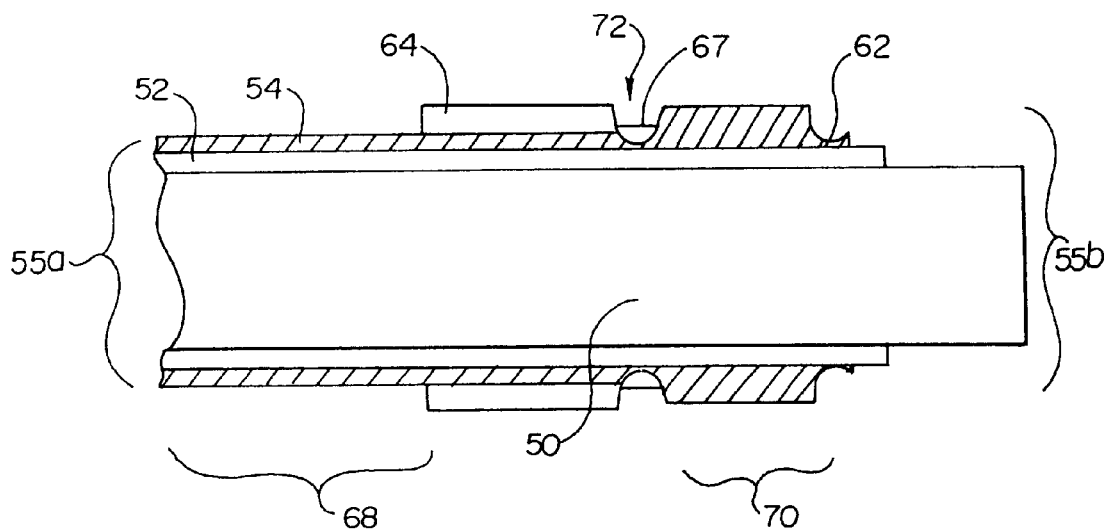
FIG. 9B shows another view similar to FIG. 9A except that it shows different means of securing the braid to the inner tubular member.
Figure 11A:
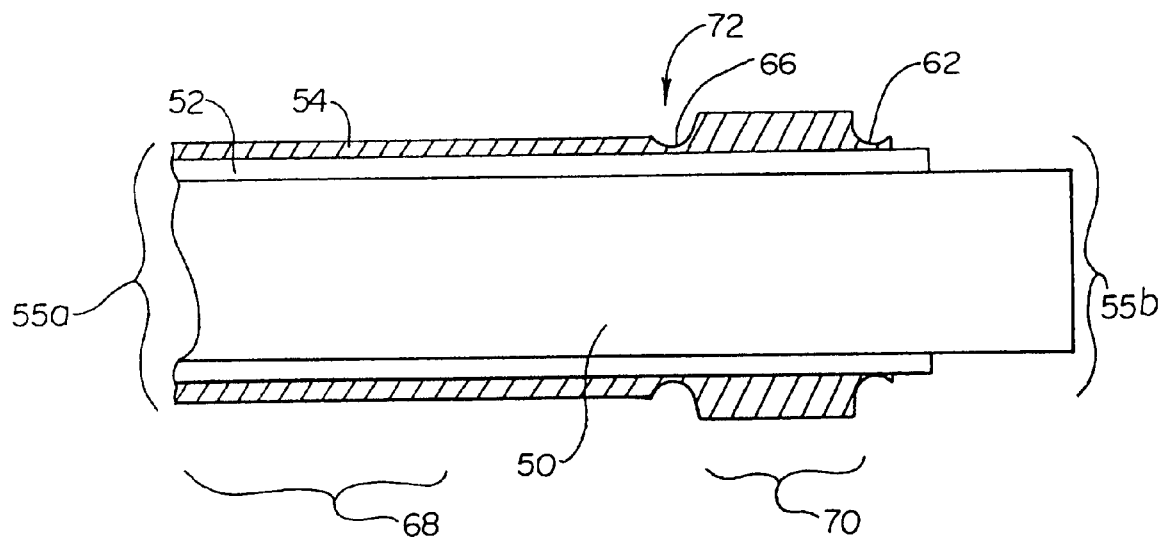
FIG. 11A shows an exaggerated view of an area of interest of FIG. 11.

FIG. 9A shows a magnified and exaggerated view of a mandrel 50 covered by an inner tubular member 52 with braid 54 partially covered by second sleeve 64. The braid 54 has a first region 68 and a second region 70 separated by the second sleeve 64, as well as an intermediate portion 72. The braid 54 has a reduced outer diameter 55a in the first region 68, and a greater outer diameter 55b in the second region 70. Part of the braid 54 in the intermediate portion 72 has been secured to the inner tubular member 52 using a UV cure adhesive or epoxy 66. It is contemplated that, rather than a UV cure adhesive or epoxy 66, a ring of heat shrink material 67 may be used to secure the braid 54 in the intermediate portion 72 to the inner tubular member 52, as shown in FIG. 9B.

Figure 10:
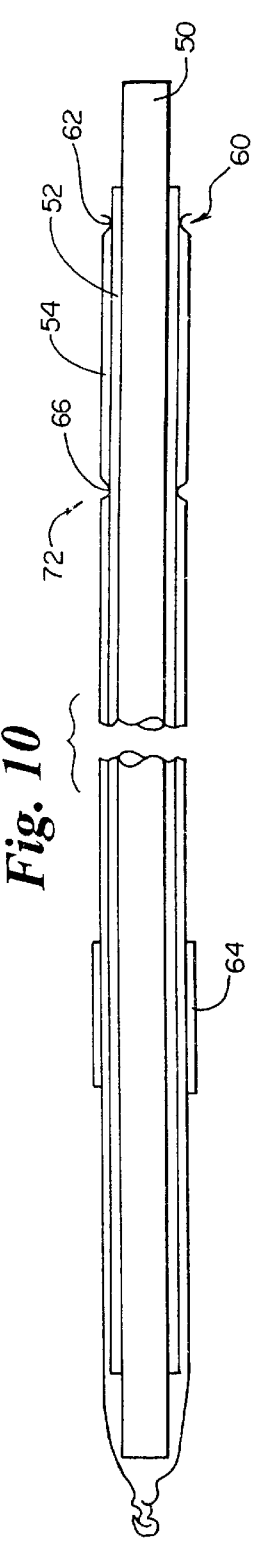
FIG. 10 shows the second diameter sleeve of FIG. 9 partially removed from the braid.
Figure 11:
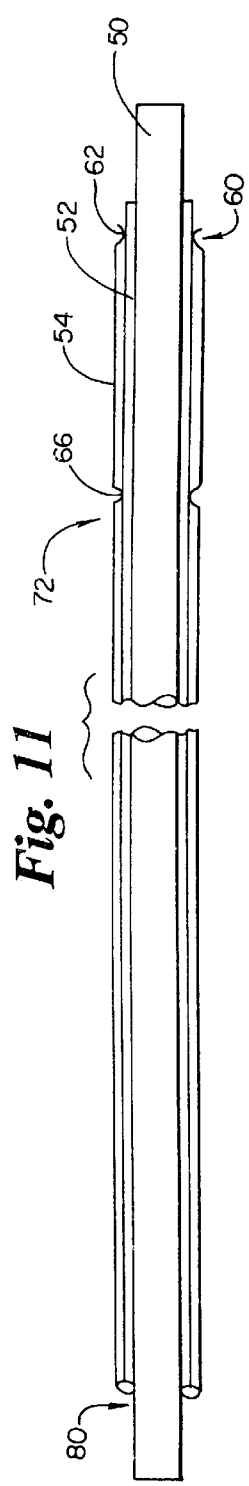
FIG. 11 shows the second diameter sleeve of FIG. 10 completely removed from the braid.

Once the intermediate portion 72 of the braid 54 is secured relative to the inner tubular member 56, the second sleeve 64 is removed. FIG. 10 shows the second sleeve 64 partially removed, and FIG. 11 shows the second sleeve 64 completely removed. At this point, the braid 54 may be secured to the inner tubular member 52 n ear the proximal en d of the inner tubular member 52, as shown at 80. The portion of the braid that is proximal to the inner tubular member 52 may then be removed. FIG. 1A shows a magnified and exaggerate d view similar to that of FIG. 11, wherein the braid 54 is shown having a lesser diameter 55a in a first region 68 and a greater diameter 55b in a second region 70.

Figure 12:
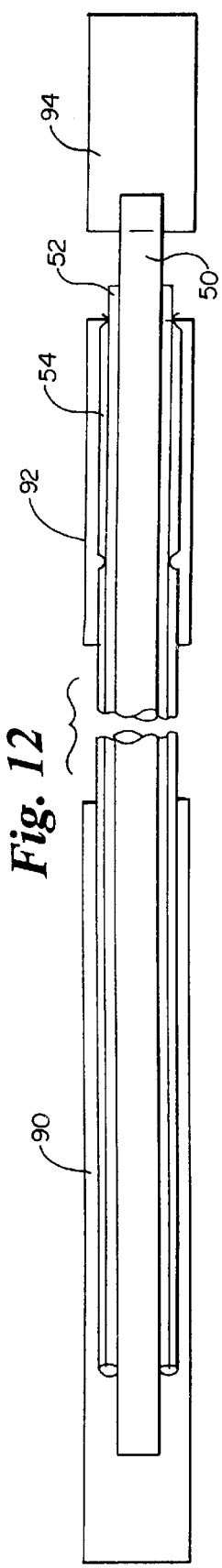
FIG. 12 shows a first outer tube, a second outer tube and a plug tube positioned over the braid of FIG. 11.

FIG. 12 shows a first outer tube 90, a second outer tube 92 and a plug tube 94 positioned over the braid 54 of FIG. 11. The first outer tube 90 and second outer tube 92 preferably have different mechanical characteristics or properties. For example, the first outer tube 90 may be less flexible than the second outer tube 92. Referring to FIG. 13, the first outer tube 90, the second outer tube 92 and the plug tube 94 are maneuvered to abut one another, and a heat shrink sleeve 100 is provided thereover. Sufficient heat is applied to cause the first outer tube 90, the second outer tube 92 and the plug tube 94 to become softened. The heat also causes the heat shrink sleeve 100 to contract. The axial and longitudinal forces of the contracting heat shrink sleeve 100 cause the first outer tube 90, the second outer tube 92 and the plug tube 94 to bond to one another. The catheter is then cooled, and the heat shrink sleeve 100 is removed. The plug tube 94 is also removed, preferably by cutting, as shown in FIG. 14. Thereafter, the mandrel 50 is removed, as shown in FIG. 15.

FIGS. 16–20 illustrate another method for forming a catheter in accordance with the present invention. In this method, the inner diameter of the braid is changed to provide one or more regions that have different braid densities. Referring specifically to FIG. 16, a mandrel 110 is shown having an inner tubular layer 112 provided thereon. The mandrel 110 is preferably made from a stainless steel, and the inner tubular member 112 is preferably made from PTFE. To increase the inner diameter of the braid, one or more rings of material may be provided circumferentially around selected regions of the inner tubular member 112. For example, a first ring or annulus 114 is provided around a first region 117 of the inner tubular member 110. Likewise, a second ring or annulus 116 is provided around a second region 118 of the inner tubular member 110. In a preferred embodiment, annulus 114 and annulus 116 are formed from PEBAX, and the outer surface of the PTFE inner tubular member 112 is chemically etched to allow improved bonding between the PTFE inner tubular member 112 and annulus 114 and annulus 116.

FIG. 17 shows a braid 120 provided over the inner tubular layer 112, annulus 114 and annulus 116. As shown, the braid 120 is not yet tensioned and therefore has a non-uniform outer diameter. The proximal end of the braid may be twisted to anchor the proximal end of the braid relative to the inner tubular member 112, as described above. The distal end 122 of the braid is then secured to the inner tubular member 112 using an adhesive 124 or a ring of heat shrink tubing, as described above.

FIG. 18 shows a perspective view of a grab washer 130 for tensioning the braid 120 of FIG. 17. The grab washer 130 preferably includes a bore 132 therethrough with a number of slits 134 extending outward from the bore 132. Between each of the slits is a flap 136. The slits 134 allow the diameter of the bore 132 to change by pushing the flaps 136 laterally from the plane of the grab washer 130.

The bore 132 of the grab washer 130 receives the distal end 128 of the catheter. The grab washer 130 is then slid proximally over the catheter such that the flaps 136 engage the braid 120, as shown in FIG. 19. The flaps tension the braid about the outer surface of the catheter. When the grab washer 130 passes over annulus 114 or annulus 116, the inner diameter of the braid increases. It has been found that it is possible to obtain a change of approximately 7 pic for each 0.001" increase in the inner diameter of the braid 54. FIG. 20 shows the braid 120 fully tensioned over the inner tubular member 112 and the two annulus rings 114 and 116.

An outer layer having a number of regions each having different mechanical properties may be provided over the braid 120. This may be done in accordance with the discussion of FIGS. 12–15 above. It is contemplated that the wall thickness of the outer layer segments may be adjusted in the regions of annulus 114 and annulus 116 so that the outer diameter of the catheter is consistent.

Having thus described the preferred embodiments of the present invention, those of skill in the art will readily appreciate the other useful embodiments within the scope of the attached claims.

What is claimed is:

1. A catheter comprising:

an inner tube having a first region and a second region, the inner tube further having an outside diameter;

a support member positioned over at least a portion of the inner tube including over the first region and the second region, the support member having a first portion that corresponds to the first region of the inner tube and a second portion that corresponds to the second region of the inner tube, the first portion of the support member having a diameter that is different from the diameter of the second portion at non-overlapping sections of the support member, wherein the difference in diameters between the first portion and the second portion varies independently with relation to the outer diameter of the inner tube.

2. A catheter according to claim 1 further comprising an outer tube positioned over the support member.

3. A catheter shaft according to claim 1 wherein the inner tube comprises:

a tube having a relatively constant outer diameter;

an annulus positioned over the inner tube at the first region.

4. A catheter according to claim 3 wherein the annulus is formed from a heat shrink material.

5. A catheter according to claim 3 wherein the inner tube is PTFE, and the annulus is polyether block amide.

6. A catheter shaft according to claim 3 wherein the annulus is secured to the inner tube at the first region.

7. A catheter comprising:

a catheter shaft having a first region and a second region, wherein the catheter shaft further includes at least an inner layer having an outside diameter and an outer layer, with the support member disposed therebetween; and a support member extending along at least a portion of the inner layer, including along the first region and the second region, the support member having a first portion that corresponds to the first region of the catheter shaft and a second portion that corresponds to the second region of the catheter shaft, the first portion of the support member having a diameter that is different from the diameter of the second portion, and wherein the difference in diameters along a portion of the catheter shaft between the first portion and the second portion varies independently with relation to the outside diameter of the inner layer.

8. A catheter according to claim 7 wherein the support member is a braid.

9. A catheter according to claim 8 wherein the first portion of the braid has an increased braid density relative to the braid density of the second portion.

10. A method for forming a catheter having an inner tube and a support member, the method comprising the steps of:

providing an inner tube having an outer diameter;

providing a support member over the inner tube;

causing a first region of the support member to have a first diameter; and causing a second region of the support member to have a second diameter, wherein the first diameter is different from the second diameter at non-overlapping sections of the support member, and wherein the difference in diameters between the first region and the second region of the support member varies independently with relation to the outer diameter of the inner tube.

11. A method for forming a catheter having an inner tube and a support member, the method comprising the steps of:

providing an inner tube having an outer diameter;

providing a support member over the inner tube;

causing a first region of the support member to have a first diameter, wherein the first region has a proximal end and a distal end;

securing the support member relative to the inner tube proximate the distal end of the first region;

causing a second region of the support member to have a second diameter, wherein the first diameter is different from the second diameter at non-overlapping sections of the support member, wherein the second region overlaps at least a portion of the first region, and wherein the difference in diameters between the first region and the second region of the support member varies independently with relation to the outer diameter of the inner tube; and securing the support relative to the inner tube proximate the distal end of the second region.

12. A method according to claim 11 wherein the support member is secured relative to the inner tube with an adhesive.

13. A method according to claim 11 wherein the support member is secured relative to the inner tube with an annulus of heat shrink tubing.

14. A method for forming a catheter having an inner tube and a support member, wherein the inner tube has a proximal end, a distal end and an outer surface, the method comprising the steps of:

sliding the support member distally over the outer surface of the inner tube;

sliding a first sleeve having a distal end over at least a portion of the support member until the distal end of the first sleeve reaches a first location, the first location being distal of the proximal end of the inner tube;

securing the support member relative to the inner tube proximate the first location;

removing the first sleeve;

sliding a second sleeve having an inner diameter that is less than the inner diameter of the first sleeve over the support member until a distal end of the second sleeve reaches a second location, wherein the second location is proximal of the first location; and securing the support member relative to the inner tube proximate the second location.

15. A method of forming a catheter having an inner tube and a support member, the method comprising the steps of:

forming an inner tube having a first region and a second region, wherein the first region and the second region have an outer diameter;

sliding the support member, having an outer diameter, distally over at least a portion of the inner tube including over the first region and the second region;

tensioning the support member against the first region and the second region, wherein the outer diameter of the support member over the first region is different than over the second region at non-overlapping sections of the support member, and wherein the difference in the support member outer diameter over the first region and the second region varies independently with relation to the outer diameter of the inner tube; and providing an outer layer over the support member.

16. A catheter shaft having a central longitudinal axis, comprising:

a first tubular section extending along a first portion of the catheter shaft and parallel to a central longitudinal axis, the first tubular section having an outer diameter, the first tubular section further including a plastic material;

a braid extending along at least a portion of the central longitudinal axis, the braid having a first region with a first braid diameter and a second region with a second braid diameter, wherein the first braid diameter is different from the second braid diameter at non-overlapping sections of the support member, and wherein the difference in diameters between the first region and the second region varies independently with relation to the first tubular section; and a second tubular section extending along a second portion of the catheter shaft and parallel to the central longitudinal axis, the second tubular section including a plastic material that has a different mechanical property than the plastic material of the first tubular section.

17. A catheter shaft according to claim 16 wherein the different mechanical property is the durometer of the plastic material.

18. A catheter shaft according to claim 16 wherein the first portion of the catheter shaft overlaps at least a portion of the first region.

* * * * *